US00PP18290P2

(12) United States Plant Patent
Hooijman

(10) Patent No.: US PP18,290 P2
(45) Date of Patent: Dec. 11, 2007

(54) ***LIMONIUM* PLANT NAMED 'ESM MIRLO'**

(50) Latin Name: *Limonium sinnuatum*
Varietal Denomination: Esm Mirlo

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 11/489,199

(22) Filed: Jul. 19, 2006

(51) Int. Cl.
*A01H 5/00* (2006.01)

(52) U.S. Cl. ..... Plt./358
(58) Field of Classification Search ..... Plt./358
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Limonium* plant named 'Esm Mirlo', characterized by its erect, long and strong flowering stems; vigorous growth habit; freely flowering habit; small purple-colored flowers; and good postproduction longevity.

1 Drawing Sheet

Botanical designation: *Limonium sinnuatum.*
Cultivar denomination: 'Esm Mirlo'.

BACKGROUND OF THE INVENTION

The present invention relates to a new and distinct cultivar of *Limonium* plant, botanically known as *Limonium sinnuatum,* grown commercially as a cut flower, and hereinafter referred to by the name 'Esm Mirlo'.

The new *Limonium* is a product of a planned breeding program conducted by the Inventor in El Quinche, Pichincha, Ecuador. The objective of the breeding program is to create new freely flowering *Limonium* cultivars with long and straight flowering stems.

The new *Limonium* originated from a open-pollination in El Quinche, Pichincha, Ecuador in August, 2000 of a proprietary selection of *Limonium sinnuatum* identified as Line 123, not patented, as the female, or seed, parent with an unknown selection of *Limonium sinnuatum.* The cultivar Esm Mirlo was discovered and selected by the Inventor as a flowering plant from within the progeny of the stated open-pollination in a controlled environment in El Quinche, Pichincha, Ecuador.

Asexual reproduction of the new *Limonium* by cuttings in a controlled environment in El Quinche, Pichincha, Ecuador since August, 2001, has shown that the unique features of this new *Limonium* are stable and reproduced true to type in successive generations.

SUMMARY OF THE INVENTION

The cultivar Esm Mirlo has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Esm Mirlo'. These characteristics in combination distinguish 'Esm Mirlo' as a new and distinct cultivar of *Limonium:*

1. Erect, long and strong flowering stems.
2. Vigorous growth habit.

3. Freely flowering habit.
4. Small purple-colored flowers.
5. Good postproduction longevity.

In side-by-side comparisons conducted in El Quinche, Pichincha, Ecuador, plants of the new *Limonium* differed from plants of the female parent selection in the following characteristics:

1. Plants of the new *Limonium* were more vigorous and had stronger stems than plants of the female parent selection.
2. Plants of the new *Limonium* were more freely flowering than plants of the female parent selection.
3. Plants of the new *Limonium* and the female parent selection differed in flower color as plants of the female parent selection have cream-colored flowers.

Plants of the new *Limonium* can be compared to plants of the *Limonium* cultivar Crystal Dark Blue, not patented. In side-by-side comparisons conducted in El Quinche, Pichincha, Ecuador, plants of the new *Limonium* differed from plants of the cultivar Crystal Dark Blue in the following characteristics:

1. Plants of the new *Limonium* had shorter internodes than plants of the cultivar Crystal Dark Blue.
2. Plants of the new *Limonium* had smaller leaves than plants of the cultivar Crystal Dark Blue.
3. Plants of the new *Limonium* were more freely flowering than plants of the cultivar Crystal Dark Blue.
4. Plants of the new *Limonium* and the cultivar Crystal Dark Blue differed in flower color.

BRIEF DESCRIPTION OF THE PHOTOGRAPHS

The accompanying photographs illustrate the overall appearance of the new *Limonium.* These photographs show the colors as true as it is reasonably possible to obtain in colored reproduction of this type. Colors in the photographs may differ slightly from the color values cited in the detailed botanical description which accurately describe the colors of the new *Limonium.*

Clockwise from the upper left photograph: side perspective view of a typical flowering stem;

close-up view of a typical inflorescence; and close-up view of upper and lower surfaces of typical leaves of 'Esm Mirlo'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown during the winter in El Quinche, Pichincha, Ecuador in ground beds in a polyethylene-covered greenhouse and under conditions and practices which approximate those generally used in commercial cut *Limonium* production. During the production of the plants, day temperatures ranged from 12° C. to 30° C., night temperatures ranged from 5° C. to 11° C. and light levels ranged from 1,000 to 1,150 foot-candles. Plants were pinched. Measurements and numerical values represent averages for typical seven-month old flowering plants.

Botanical classification: *Limonium sinnuatum* cultivar Esm Mirlo.

Commercial classification: Cut flower *Limonium.*

Parentage:

*Female, or seed, parent.*—Proprietary selection of *Limonium sinnuatum* identified as Line 123, not patented.

*Male, or pollen, parent.*—Unknown selection of *Limonium sinnuatum,* not patented.

Propagation:

*Type.*—By cuttings.

*Time to initiate roots.*—About 20 days at 30° C. to 35° C.

*Time to produce a rooted cutting.*—About five to six weeks at 25° C. to 30° C.

*Root description.*—Fine, fibrous; N199D in color.

Plant description:

*Appearance.*—Perennial subshrub grown as a cut flower. Erect and strong flowering stems; inverted triangle form. Leaves basal. Freely flowering habit; numerous flowers arranged in symmetrical and moderately dense compound panicles. Vigorous growth habit.

*Branching habit.*—After pinching, about 80 flowering stems develop per year.

*Plant height.*—About 110 cm.

*Plant diameter or spread.*—About 54 cm.

*Flowering stems.*—Length: About 105 cm. Diameter: About 6 mm. Internode length: About 6.7 cm. Strength: Strong. Texture: Pubescent. Color: 139A.

Foliage description:

*Arrangement.*—Alternate, simple; sessile.

*Length.*—About 24.8 cm.

*Width.*—About 4.9 cm.

*Shape.*—Narrowly obovate.

*Apex.*—Acute to obtuse.

*Base.*—Attenuate.

*Margin.*—Crenate, sinuate; undulate.

*Texture, upper and lower surfaces.*—Pubescent.

*Venation pattern.*—Pinnate.

*Color.*—Developing foliage, upper and lower surfaces: 143A. Fully expanded foliage, upper surface: 137A; venation, 147D. Fully expanded foliage, lower surface: 137B; venation, 146C.

Flower description:

*Flower arrangement and habit.*—Compound cymes with numerous flowers; flowers actinomorphic and symmetrical. Very freely flowering, about 1,100 flowers per inflorescence. Flowers face mostly upright.

*Flowering response.*—In Ecuador, plants flower year round. Plants begin flowering about 17 weeks after planting.

*Post-production longevity.*—As a cut flower, flowers last for about two weeks. Corolla self-cleaning; calyx persistent.

*Fragrance.*—None detected.

*Inflorescence height.*—About 103 cm.

*Inflorescence diameter.*—About 34 cm.

*Flower diameter.*—About 6.5 mm.

*Flower depth (height).*—About 1.4 cm.

*Flower buds.*—Length: About 6 mm. Diameter: About 1 mm. Shape: Ellipsoidal. Color: Apex: 77B. Midsection: 149D. Base: 144B.

*Corolla.*—Petals per flower: Five. Petal length: About 1.2 cm. Petal width: About 3 mm. Petal shape: Triangular. Petal apex: Emarginate. Petal margin: Entire. Petal texture, upper and lower surfaces: Smooth, glabrous; membraneous. Petal color: When opening, upper and lower surfaces: 149D; towards the base, close to 155D. Fully opened, upper and lower surfaces: 157C; towards the base, close to 155D.

*Calyx.*—Sepals per flower: Five. Length: About 1.4 cm. Width: About 9 mm. Shape: Salverform. Sepal apex: Fringed. Sepal margin: Entire. Sepal texture, upper and lower surfaces: Smooth, glabrous. Sepal color: When opening, upper surface: 83D; throat, 149D. When opening, lower surface: N81B, tube, 145D. Fully opened, upper surface: 84D; throat, 144B. Fully opened, lower surface: N81C; tube, N144D.

*Pedicels.*—Length: About 33 cm. Diameter: With wings, about 1.5 cm; without wings, about 6 mm. Strength: Strong. Angle: About 32° from vertical. Texture: Smooth, glabrous. Color: 139A.

*Reproductive organs.*—Stamens: Quantity per flower: Five. Anther shape: Rounded. Anther length: About 1 mm. Anther color: 154D. Pollen amount: Abundant. Pollen color: 154D. Pistils: Quantity per flower: One. Pistil length: About 9 mm. Style length: About 7 mm. Style color: Close to 155D. Stigma shape: Filiform. Stigma color: Close to 155D. Ovary color: 144D.

*Seeds.*—Seed development has not been observed.

Disease/pest resistance: Plants of the new *Limonium* have been observed to be resistant to *Botrytis.* Plants have not been shown to be resistant to pests and other pathogens common to *Limonium.*

Temperature tolerance: Plants of the new *Limonium* have been observed to tolerate temperatures ranging from about 5° C. to about 40° C.

It is claimed:

1. A new and distinct *Limonium* plant named 'Esm Mirlo' as illustrated and described.

* * * * *

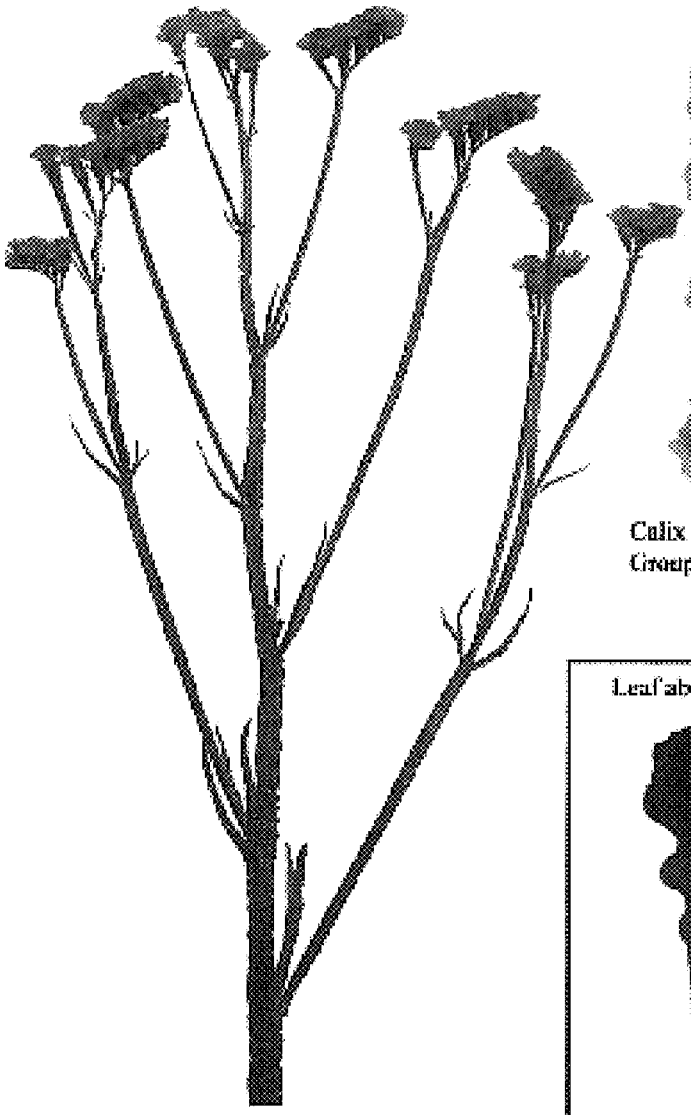
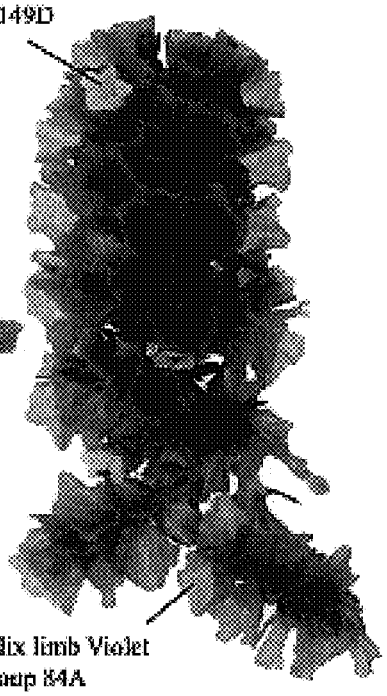
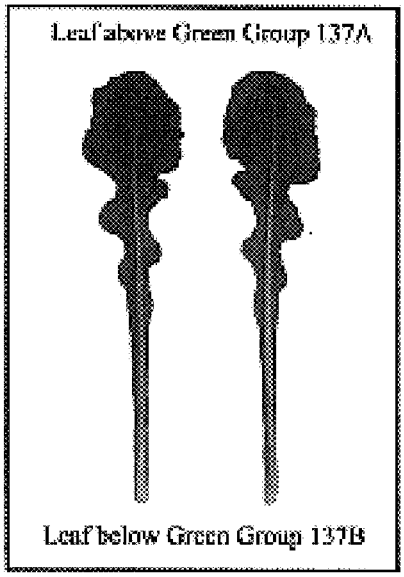

Esm Mirlo